United States Patent [19]

Nilsson

[11] Patent Number: 5,010,599
[45] Date of Patent: Apr. 30, 1991

[54] PORTABLE UNISEX URINAL

[76] Inventor: Leif Nilsson, Blåbärsvägen 1, S-260 40 Viken, Sweden

[21] Appl. No.: 134,942

[22] Filed: Dec. 18, 1987

[30] Foreign Application Priority Data

Mar. 30, 1987 [SE] Sweden .................... 8701299

[51] Int. Cl.⁵ .............................................. A61G 9/00
[52] U.S. Cl. ..................................... 4/144.2; 4/144.3; 604/317
[58] Field of Search .................. 4/144.1, 144.2, 144.3, 4/144.4, 114.1; 137/854, 855; 128/760, 761; 604/345, 346, 347, 331, 347, 353, 317

[56] References Cited

U.S. PATENT DOCUMENTS

| | | | |
|---|---|---|---|
| 1,768,638 | 7/1930 | Sheats | 137/854 |
| 3,432,865 | 6/1967 | Schwartz | 4/144.2 |
| 3,568,218 | 3/1971 | Beckman | 4/144.1 |
| 3,703,731 | 11/1972 | Leiser | 4/144.3 |
| 3,990,439 | 11/1976 | Klinger | 137/854 |
| 4,270,231 | 6/1981 | Zint | 4/144.4 |
| 4,401,224 | 8/1983 | Alonso | 137/854 |
| 4,846,816 | 7/1989 | Manfredi | 604/331 X |

FOREIGN PATENT DOCUMENTS

| | | | |
|---|---|---|---|
| 865415 | 2/1953 | Fed. Rep. of Germany | 137/854 |
| 2634071 | 2/1978 | Fed. Rep. of Germany | 4/144.4 |
| 2061103 | 5/1981 | United Kingdom | 4/144.1 |
| 2088023 | 6/1982 | United Kingdom | 137/854 |
| 8103273 | 11/1981 | World Int. Prop. O. | 604/347 |

Primary Examiner—Henry J. Recla
Assistant Examiner—Robert M. Fetsuga
Attorney, Agent, or Firm—Kane, Dalsimer, Sullivan, Kurucz, Levy, Eisele and Richard

[57] ABSTRACT

A portable unisex urinal comprises a urine tube provided with a first and a second aperture, the first aperture being intended to form a urine inlet end and being so shaped as to enable it to be used by both men and women, a urine bag having an inlet end and an openable and closable outlet end, a valve which includes a cylindrical valve body, one end of which is intended to co-act in a liquid-tight manner with the second aperture, and the other end of which is intended to co-act with the inlet end of the urine bag. At least the valve and the urine bag form an undivided and liquid-tight urine collecting device. Alternatively, the urine tube, valve and urine bag together form an undividable or inseparable assembly. The valve also incorporates a liquid and vapor impervious diaphragm.

9 Claims, 1 Drawing Sheet

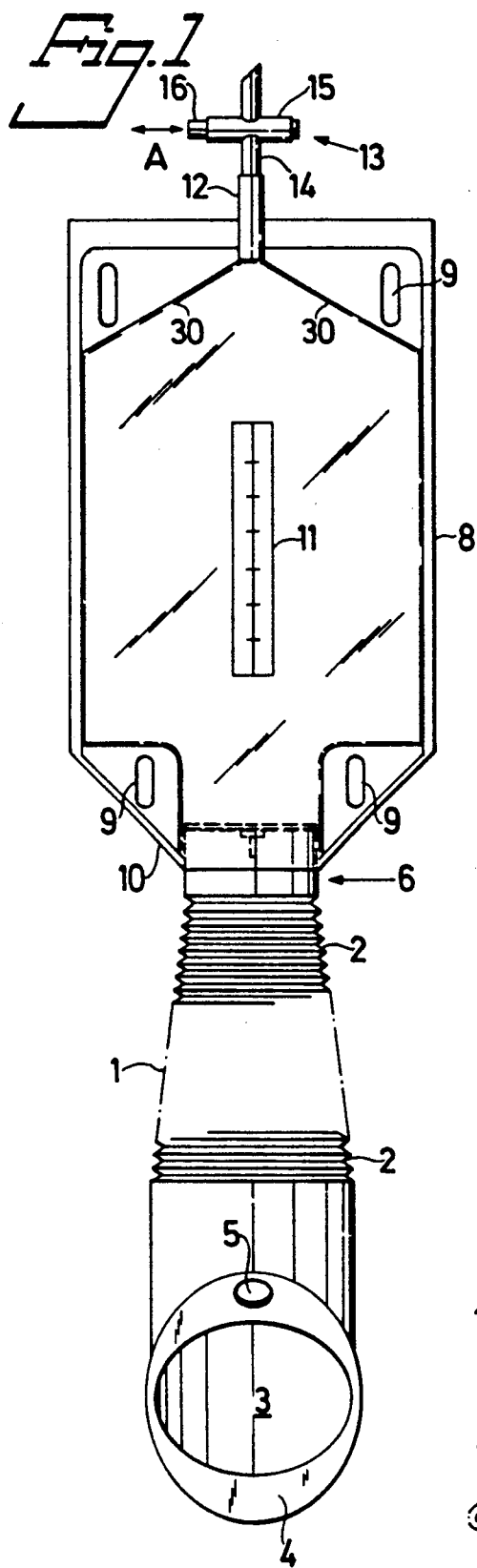
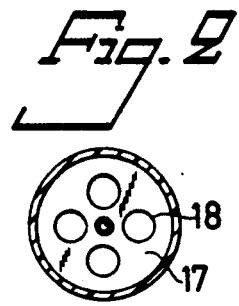
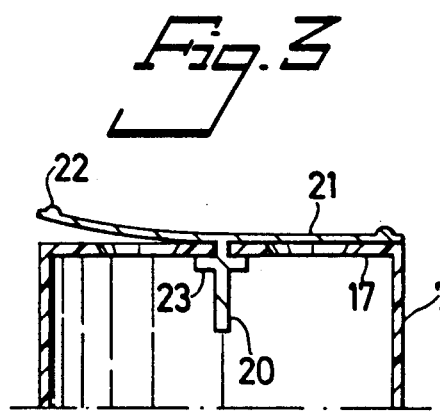
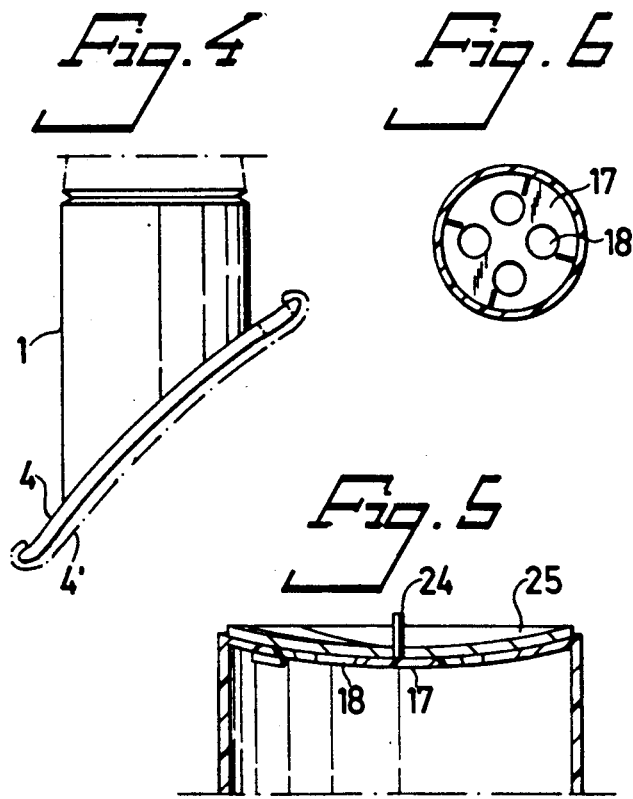

PORTABLE UNISEX URINAL

The present invention relates to a portable unisex urinal.

Portable urinals intended for use by a patient, people who are incapacitated or sick, e.g. bed-ridden patients or persons who suffer from incontinence, are known to the art. The most common of these urinals are in the form of glass urine bottles or plastic urine bottles which are resistant to uric acid. These known urinals, however, are relatively expensive and must be sterilized each time after use. Patients who are required to lie in an incumbent position may find it difficult to manipulate or handle urinals of this kind. Furthermore, subsequent to its use, the bottle must be removed from the patient's bed and the contents of the bottle emptied by ward staff, at the earliest opportunity. In the case of hospital patients who are obliged to lie on their stomachs, the matter of urinating is troublesome and relatively time consuming, on the part of both the patient and the ward staff. Normally, it requires three members of the ward staff to lift and turn such a patient. Furthermore, because the urine bottles are constantly open at one end thereof, bacteria is able to escape to the surrounding atmosphere.

Consequently, a prime object of this invention is to provide a portable urinal which can be used effectively by both sexes, while in a recumbent position.

A further object is to produce such a unisex urinal which can be carried easily without undue strain and without liquid escaping from the urinal, irrespective of its position.

Still another object is to provide a unisex urinal which will seal automatically against the undesirable emission of harmful vapours from the urine present in the urinal.

Yet another object is to provide a portable unisex urinal which can be manufactured readily in large numbers and at low costs, therewith rendering the urinal viable as a throw-away item.

Still a further object of the invention is to provide a portable unisex urinal in which a urine tube can be bent to any selected angle in relation to a fixed axis.

Accordingly, this invention concerns a portable unisex urinal which comprises a flexible urine tube having located at one end thereof a first aperture means, the configuration of which is such as to accommodate the organs of both men and women, and second aperture means located at the other end of said tube; a urine collecting bag having an inlet end, which is connected sealingly to the second aperture means, and an openable end; and check valve means located in the region of the junction between the second aperture means of the flexible urine tube and the inlet end of the urine bag, said check valve means incorporating means for preventing the escape of vapour from the contents of the urine bag.

According to one preferred embodiment of the inventive unisex urinal, the check valve means comprises a cylindrical valve body which is fully open at one end thereof and which has provided at the other end thereof a bottom member in which there is formed a given number of holes. The perforated bottom member is covered by a pressure-activated diaphragm which is impermeable to liquid and also to bacteria and which sealingly covers the holes in the bottom of the valve body in the absence of pressure on the valve in a direction towards the bag. Movement in the diaphragm relative to the perforated bottom member is guided by a pin located centrally on the bottom member, and the rim area of the diaphragm is preferably thicker than the central area thereof, so as to accelerate movement of the diaphragm towards its valve closing position when pressure on the diaphragm is relieved.

These and other features of the invention, together with advantages afforded thereby, will become more apparent from the following description of a preferred embodiment, made with reference to the accompanying drawings, in which FIG. 1 illustrates the inventive unisex urinal from above;

FIG. 2 is a sectional view taken on the line A—A in FIG. 1;

FIG. 3 is a sectional view taken on the line B—B in FIG. 2.

FIG. 4 is a side view of the open end of the urinal;

FIGS. 5 and 6 illustrate respective modified embodiments of the inventive unisex urinal and correspond to the components illustrated in FIGS. 2 and 3.

DESCRIPTION OF A PREFERRED EMBODIMENT

The following description of the inventive unisex urinal is made with reference to the urinal when in use. Consequently all positional references are made with regard to the in-use position of the urinal.

The illustrated portable urinal comprises a urine tube 1 which is made of a relatively rigid plastics material and which has provided at one or more locations along its length bellows-like or pleated areas 2 which allow the tube to be bent or otherwise deflected plastically to selected angular positions in relation to a fixed axis. The tube has at one end a first aperture means, or inlet 3 which is of oval configuration such as to form a so-called vagina-cup which can be fitted to the vagina of a female patient for instance. The first aperture means or inlet 3 has provided therearound a cuff 4 which extends approximately at right angles to the long axis of the urine tube 1. The inlet aperture 3 of the tube 1 may be fitted with a cover 4' as indicated by a chain line in FIG. 4, so as to enable the inlet aperture to be closed. The reference 5 in FIG. 1 illustrates a hole by means of which the urinal can be hung when not in use. The illustrated urine tube tapers symmetrically, e.g. may be conical, such that the diameter of the tube at the end thereof incorporating the inlet aperture 3 is larger than the diameter of the other end of the tube. It will be seen from FIG. 4 that the end of the tube 1 incorporating the inlet aperture 3 may be bevelled. It will be understood that the oval configuration of the inlet aperture will enable the urinal to be used comfortably by both men and women.

The end of the urine tube 1 distal from the inlet aperture 3 is joined to a valve means, generally referenced 6, which comprises a cylindrical valve body 7 which is made of an inflexible or relatively inflexible plastics material. Naturally, the valve means need not necessarily be cylindrical, since an equivalent valve action can be obtained with valve bodies of other configurations.

The open end of a urine bag 8 is intended to be fitted around the cylindrical valve body 7 and to be bonded thereto, e.g. heat welded thereto, so as to form an inseparable unit with said valve body. The rim of the urine bag 8 preferably lies flush with the illustrated upper end surface of the cylindrical valve body 7, and a liquid-tight connection is created between the inner wall of the bag and the outer wall of the valve, in a manner hereinafter described.

The urine bag 8 together with its associated valve means 6 is then inserted into the urine tube 1 with a press fit, so that the urine tube encloses the whole of the valve means 6 or at least a major part of said housing. A liquid-tight join can be obtained between the urine tube on the one hand and the valve/urine bag on the other, for example by applying heat such as to cause the material of the valve body/urine bag to flow out. It is also conceivable, when assembling the urine tube to the urine bag/ valve unit to insert the tube 1 into the cylindrical valve body 7 so that the valve body encloses the urine tube 1. An integrated leakage-free unit can also be achieved in this case, by applying heat to the various assembled components thereof.

The urine bag 8 is also made of plastics material, although of a thinner gauge, and therewith a softer material than the material of the urine tube 1. As shown in FIG. 1 that part of the urine-bag structure located adjacent the valve body 7 has holes 9 provided therein for hanging the bag on a suitable support. The bag also has obliquely shaped corners 10 and a graduated scale 11. Holes 9 for hanging the bag onto a suitable support are also provided in the lower part of the urine bag structure. Located in the lower or bottom part of the urine bag construction is an opening for accommodating a urine drainage pipe 12. The pipe 12 co-acts with a valve arrangement, generally referenced 13, in which a further pipe 14 inserted into the pipe 12 is connected with a transverse pipe 15 in which a peg 16 can be moved axially, in the direction of the arrow A, in order to open or close the connection with the urine bag 8. It will be understood, however, that any suitable valve arrangement can be used to this end.

The bottom or lower part of the illustrated urine bag is also shaped obliquely (at 30) so that the bag slopes down towards the opening and thus towards the drainage pipe 12. This will ensure that the entire contents of the urine bag 8 will be emptied, without risk of any urine remaining in the bag.

The check valve means 6 enables the urinal to be handled and carried without risk of urine flowing back from the urine bag and out through the urine tube 1. In addition hereto the valve means 6 is also constructed so as to be impervious to any harmful bacteria that might develop in the urine contained in the bag, or carried by the urine from the body of the patient. The valve means can also be constructed to prevent urine vapour from escaping from the collecting device.

A first embodiment of such a valve means is illustrated in FIG. 2 and 3.

The valve body 7 of the illustrated valve means has a valve bottom 17 in which four openings 18 are formed symmetrically around the centre axis of the bottom, these openings being of conical shape, i.e. tapering in a direction towards the urine tube 1. In order to enable the urine flowing through the urine tube 1 to pass readily into the valve means 6, the openings 18 have a relatively large size and are spaced from the wall of the valve means. A centrally located guide pin 20 is passed sealingly through an opening in the valve bottom 17 of the valve means 6. The guide pin 20 is firmly connected to a thin, liquid and vapour impermeable diaphragm 21 which in a valve closing position lies against the surface of the valve means 6 facing inwardly towards the urine bag 8, therewith preventing the through passage of urine and urine vapour. The diaphragm 21 is dimensioned to cover the whole of the bottom 17 of the valve body 7, and thus extends out to the outer edge of the body 7, as illustrated in FIG. 3. The diaphragm is preferably thickened in the vicinity of its periphery and to this end the illustrated diaphragm has provided on its periphery an annular bead 22 which is operative in distributing liquid-pressure uniformly around the diaphragm. An additional function of the bead 22, or like thickening, is to facilitate the return of the diaphragm to its valve closing position when pressure is removed from the diaphragm, as hereinafter explained. Thus, as urine flows through the tube 1 and passes through the holes 18, it exerts pressure in the diaphragm 21, which is therewith lifted radially and progressively in a direction away from the wall of the valve body 7 inwardly towards the centre, the extent to which the diaphragm is raised angularly in this way being contingent on the pressure and/or the quantity of the liquid present. This function of the valve means is illustrated in FIG. 3. It will also be seen from FIG. 3 that the guide pin 20 has a stop means 23 which prevents movement of the diaphragm 21 in the axial direction of the tube. The conicity of the holes 18 ensures optimum sealing of the diaphragm 21 against said holes. It will also be understood that the diaphragm is relatively springy and that the guide pin acts in the manner of a holding down tool which prevents the central part of the diaphragm from being raised to the same extent as the outer peripheral part thereof. FIGS. 5 and 6 illustrate a second embodiment of the valve means, in which the valve bottom 17 is slightly convex (this convex shape of the valve bottom 17 has been exaggerated in FIG. 5). In the case of the second embodiment, the bottom part of the valve body 7 facing towards the urine bag 8 has a centrally located guide pin 24 which preferably extends over the horizontal plane of the valve body. The guide pin 24 carries a diaphragm 25 which is dimensioned to cover effectively the drainage holes 18 in the valve bottom 17. The valve bottom 17 of this embodiment curves inwardly towards the imagined flow direction. The conicity of the drainage holes 18 ensures that the diaphragm will lie sealingly against the bottom of the valve means 6.

It has been found that, in addition to being inexpensive in manufacture, the valve means constructed in accordance herewith ensures that a highly efficient sealing effect is obtained. Tests were carried out on the inventive valve means, by causing liquid to run through the urine tube 1. The diaphragm 25 opened in response to the pressure exerted by the liquid, and liquid flowed down into the urine bag 8. The thin diaphragm 25 returned to its sealing abutment with the valve bottom as soon as all liquid had passed through. The liquid filled bag 8 was then turned upside down, i.e. so that the diaphragm was subjected to the weight of the overlying liquid. No leakage could be observed. It has been found that silicone rubber is a highly suitable material with regard to the diaphragm 25.

As beforementioned, the inventive urinal is intended for one-time use only. The configuration of the inlet aperture 3 and the general construction of the device enables it to be used effectively by both men and women. The flexible zone or zones on the urine tube 1 enable the tube to be bent to almost any desired angle, such that the urinal can be used with the patient in a sitting, standing or lying position. Because of the construction of the valve means 6, the urinal can always be handled and carried without risk of urine flowing back through the urine tube 1, while vapours emanating from the urine in the bag are prevented from escaping by the vapour impervious diaphragm. The urine bag 8 can be given a suitable volumetric capacity, such as to enable the urinal to be easily handled and carried. The urine is emptied through the drainage or emptying arrangement 13, and the urinal can be destructed in a conventional manner. It has been calculated that the costs of purchasing and utilizing the inventive unisex urinal are below the costs entailed by conventional handling of urine bottles and similar devices. The inventive urinal is also advantageous from a medical aspect, since exiting of bacterial florance in the urine to the ambient air is optimally restricted.

The portable unisex urinal according to the invention may be constructed to form an inseparable unit or assembly, or alternatively the urine bag and valve means can be joined together to form a inseparable unit and the urine tube fitted to said unit by the nursing staff concerned.

I claim:

1. A disposable device for collecting and temporarily storing urine of an individual of either sex, said device comprising a combination of:
   (a) a urine tube which has first and second openings, of which the first opening forms a urine inlet end of said tube and the second opening serves as a urine outlet, wherein the first opening is larger than the second opening, and wherein the tube has provided at a location along its length means which enable the tube to be bent plastically to a desired curved configuration;
   (b) a urine collecting bag which is made of a flexible material and which has an inlet end and an openable outlet end, said bag having a bottom portion which converges in a direction towards the outlet opening;
   (c) a valve means which includes a valve body which in longitudinal section is of U-shape, a proximal end which communicates with the urine tube, and a distal end which communicates with the urine collecting bag, wherein the distal end of the valve body is embraced by the upper open end of the bag to establish communication between the valve means and said bag, wherein the valve means together with the urine collecting bag form a unit, wherein the outer surface of the distal end of the valve body lies sealingly against the inner wall of the urine tube in the region of its second opening, wherein the distal end of the valve body is fitted with a liquid and vapor impermeable diaphragm which deflects downwardly under the influence of liquid pressure directed towards the bag to permit liquid to flow into the bag, wherein the distal end of the valve body has arranged therein a perforated bottom against the undersurface of which the diaphragm seats in normal use of the device, perforations in said bottom being conically tapered and the diaphragm being sufficiently resilient to return the diaphragm to position sealingly against said perforations after liquid passes to seal the valve body against back-flow of liquid, gas, odor, or bacteria and wherein seating of the diaphragm on said bottom is guided by a centrally located guide means that holds the center of the diaphragm substantially in the center of the perforations; and
   (d) a lid to close the first closable opening of urine tube (a).

2. A device according to claim 1, wherein perforations in the bottom of the valve means are arranged concentrically around the center of the bottom part, and wherein liquid entering from the urine tube is caused to flow through said perforations and cause the diaphragm to deflect downwardly while supported by the central guide means.

3. A device according to claim 1, wherein the bottom of the valve housing has openings which taper conically towards the urine tube.

4. A device according to claim 1, wherein the bottom of the valve means curves inwardly towards the urine tube, and wherein a peg or pin fixedly connected to the bottom part or the valve means forms a diaphragm guide means.

5. A device according to claim 1, wherein the diaphragm includes a circular bead which is intended to distribute the weight acting on the diaphragm.

6. A device according to claim 5, wherein the circular bead is located on or contiguous with the rim of the diaphragm and is made of the same material as said diaphragm.

7. A device according to claim 1, wherein the urine tube has bellows-like folds along its length.

8. A disposable device for collecting and temporarily storing urine of an individual of either sex, said device comprising a combination of:
   (a) a urine tube which has first and second openings, of which the first opening forms a urine inlet end of said tube and the second opening serves as an outlet, wherein the first opening is larger than the second opening, and wherein the tube has provided at a location along its length means which enable the tube to be bent plastically to a desired curved configuration;
   (b) a urine collecting bag which is made of a flexible material and which has an inlet end and an openable outlet end, said bag having a bottom portion which converges in a direction towards the outlet opening; and
   (c) a valve means which includes a valve body which in longitudinal section is of U-shape and one end of which communicates with the urine tube and the other end of which communicates with the urine collecting bag, wherein the valve body is embraced by the upper open end of the bag to establish fluid communication between the valve means and said bag, wherein the outer surface of the valve body embraced by the upper, open end of the bag lies sealingly against the inner wall of the urine tube in the region of its second opening, wherein the end of the valve means communicating with the urine bag is fitted with a diaphragm which deflects downwardly under the influence of liquid pressure directed towards the bag and permits liquid to flow into the bag but prevents liquid from flowing in the opposite direction, wherein the end of the valve means which communicates with the collecting bag has arranged therein a perforated bottom against the under surface of which the diaphragm seats in normal use of the device, wherein seating of the diaphragm on said bottom is guided by a centrally located guide means, wherein perforations in the bottom of the valve means are arranged concentrically around the center of the bottom part, and wherein liquid entering from the urine tube is caused to flow through said perforations and cause the diaphragm to deflect downwardly while supported by the central guide means.

9. A disposable device for collecting and temporarily storing urine of a male or female individual, said device comprising a combination of:

(a) a urine tube having a first closable opening which forms a urine inlet and a second opening which forms a urine outlet, wherein the first opening is larger than the second opening and wherein the tube has means along its length which enable the tube to be bent plastically to a desired curved configuration to position the first opening adjacent the individual to receive urine;

(b) a urine collecting bag made of flexible material having an upper inlet and a lower outlet, said bag having a bottom portion which slopes toward the outlet and the lower outlet has closable means thereon;

(c) a valve unit comprising a cylindrical valve means having a valve body positioned thereon, wherein a proximal end end of the valve body communicates with the urine outlet of the urine tube and a distal end of the valve body communicates with the inlet of the urine collecting bag, such that there is fluid communication between said urine tube and said bag, wherein the outer surface of the distal end of the valve body lies sealingly against the inner wall of the urine tube in the region of its urine outlet, wherein the distal end of the valve body comprises a vapor and liquid impermeable diaphragm which deflects downwardly under the influence of liquid pressure directed towards the bag and permits liquid to flow into the bag, wherein the distal end of the valve body has arranged therein a perforated bottom against the undersurface of which the diaphragm seats in normal use of the device, wherein seating of the diaphragm on said bottom is guided by a centrally located guide means that holds the center of the diaphragm substantially in the center of the perforations, wherein conically tapered perforations in the bottom of the valve means are arranged concentrically around the center of the bottom part, wherein liquid entering from the urine tube is caused to flow through said perforations and cause the diaphragm to deflect downwardly while supported by the central guide means, and wherein the diaphragm is sufficiently resilient to return the diaphragm to position sealingly against said performations after liquid passes to seal the valve against flow-flow or liquid, gas, odor, or bacteria; and (d) a cover to close the first closable opening of urine tube (a).

* * * * *